(12) United States Patent
Lohr

(10) Patent No.: US 6,271,420 B1
(45) Date of Patent: *Aug. 7, 2001

(54) PREPARATION OF QUINONEDIIMINES FROM PHENYLENEDIAMINES USING HYDROGEN PEROXIDE AND A CATALYST

(75) Inventor: Raymond A. Lohr, Avon, OH (US)

(73) Assignee: Flexsys America LP, Akron, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/552,777

(22) Filed: Apr. 21, 2000

Related U.S. Application Data

(63) Continuation of application No. PCT/US98/22805, filed on Oct. 27, 1998.

(60) Provisional application No. 60/063,764, filed on Oct. 29, 1997.

(51) Int. Cl.$^7$ .................................................. C07C 249/00
(52) U.S. Cl. ............................................................. 564/248
(58) Field of Search ............................................. 564/248

(56) References Cited

U.S. PATENT DOCUMENTS

| 5,118,807 | * | 6/1992 | Wheeler | 544/197 |
| 5,189,218 | * | 2/1993 | Desmurs et al. | 564/272 |

* cited by examiner

*Primary Examiner*—Samuel Barts
(74) *Attorney, Agent, or Firm*—Louis A. Morris

(57) ABSTRACT

A phenylenediamine compound can be converted, with high selectivity, into its corresponding quinonediimine by reacting the phenylenediamine with hydrogen peroxide in the presence of a catalyst.

22 Claims, No Drawings

PREPARATION OF QUINONEDIIMINES FROM PHENYLENEDIAMINES USING HYDROGEN PEROXIDE AND A CATALYST

This application is a Continuation of International Patent Application No. PCT/US98/22805, filed on Oct. 27, 1998, which claims priority to the filing date of U.S. Provisional Application No. 60/063,764, filed Oct. 29, 1997.

FIELD OF THE INVENTION

This invention relates to a process for preparing quinonediimines from their corresponding phenylenediamines using hydrogen peroxide in the presence of a catalyst.

BACKGROUND OF THE INVENTION

The class of cyclic enones is well known in organic chemistry. Best known examples of cyclic enones are quinones such as, for example, the benzoquinones, naphthoquinones, anthraquinones, phenanthraquinones, and the like. 1,4-Benzoquinone is commonly referred to as quinone. Quinones are generally brightly colored compounds and have versatile applications in chemical synthesis, biological uses, as redox materials, as well as in industry. There are several review articles on the chemistry and applications of quinones including, for example, *Kirk-Othmer Encyclopedia of Chemical Technology*, Third ed., Vol. 19, pages 572–605, John Wiley & Sons, New York, 1982.

The synthesis of quinones is well documented. See, for example, J. Cason, *Reactions of Benzoquinones by Oxidation, in Organic Synthesis*, Vol. IV, page 305, John Wiley & Sons, New York (1948). Quinones generally are prepared by oxidizing the appropriately disubstituted aromatic hydrocarbon derivatives, the substituents being hydroxyl or amino groups in the ortho or para positions. 1,4-Benzoquinone, for example, can be made from the oxidation of hydroquinone, p-aminophenol or p-phenylenediamine, or from quinic acid. The reagents generally used for the oxidation are dichromate/sulfuric acid mixture, ferric chloride, silver (II) oxide or ceric ammonium nitrate. In these cases, oxidation of the aminoaromatic compound is accompanied by hydrolysis to the corresponding quinone. Some processes may take several hours for completion of the reaction.

Thus, some of the prior art processes utilize a catalytic agent to achieve an acceptable reaction rate while other processes proceed without catalysts. The process according to the present invention utilizes hydrogen peroxide in the presence of a catalytic agent which provides extremely high conversion, high selectivity, and fast reaction rates to prepare the quinonediimine.

A prior art process which utilizes a catalyst in the preparation of a quinoneimine compound is disclosed by Desmurs, et al. in U.S. Pat. No. 5,189,218. The process of Desmurs, et al., which converts N-(4-hydroxyphenyl)aniline into N-phenylbenzoquinone-imine, utilizes a manganese, copper, cobalt, and/or nickel compound as a catalyst in an oxidation type reaction.

Other processes are known which use oxidizing agents to convert phenylenediamines into their corresponding quinonediimines. For example, EP 708,081 (Bernhardt et al), which describes the conversion of phenylenediamines to phenylenediimines by oxidation of the diamine in an alkali/alcoholic solution, gives a general description of such processes in its background. The EP '081 process suffers from various disadvantages including long reaction times and low yields. Additional oxidation conversion processes are described by Wheeler in U.S. Pat. No. 5,118,807 and by Haas et al, in EP 708,080. However, the use of a hydrogen peroxide in the presence of a catalytic agent in the conversion of diamino compounds to give highly selective yields of diimino compounds has not heretofore been suggested.

As such, the current invention is based on the problem of providing a simple and economic process for the preparation of N,N'-disubstituted quinonediimines in high yields and with high purity.

SUMMARY OF THE INVENTION

It has been discovered that phenylenediamine compounds can be converted with extremely high selectivity into the corresponding quinonediimine by reaction of the diamine with hydrogen peroxide in the presence of a catalytic agent. Conditions are revealed in which nearly quantitative yields have been obtained.

In contrast to prior art, an advantage of the present invention is that the conversion of phenylenediamine to the corresponding quinonediimine is nearly quantitative. Thus, very little waste material remains upon completion of the reaction.

Another advantage is that the hydrogen peroxide/catalytic agent combination, as set forth herein, provides an extremely high conversion, high selectivity and faster more complete reaction compared to prior art processes.

Still further advantages of the present invention will become apparent to those skilled in the art upon reading and understanding the following detailed description of the preferred embodiments.

DETAILED DESCRIPTION OF THE INVENTION

The object of the present invention is to provide an effective process for converting phenylenediamines into their corresponding quinonediimines.

In accordance with the object of the invention, a phenylenediamine (ortho or para) according to Formula I:

Formula I

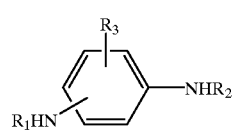

wherein $R_1$, $R_2$ and $R_3$ are the same or different radicals selected from hydrogen, hydroxyl, halogen, alkyl, alkoxy, aryl, aralkyl, alkaryl, cycloalkyl, heterocycle, acyl, aroyl, carbamyl, carboxylic acids, esters, ethers, ketones, alcohols, thiols, alkylthiols, and cyano, is reacted with hydrogen peroxide in the presence of a catalytic agent.

The reaction produces a corresponding quinonediimine according to Formula IIa or IIb:

Formula IIa

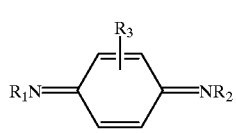

Formula IIb

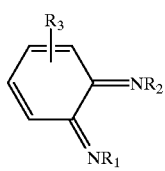

wherein R₁, R₂ and R₃ are the same as in the compound according to Formula I.

The reaction is represented as follows:

Reaction Scheme 1

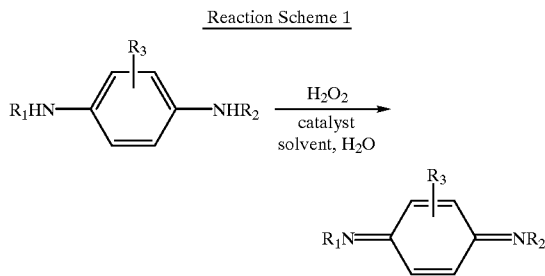

Examples of satisfactory radicals for $R_1$, $R_2$ and $R_3$ are linear or branched alkyls such as methyl, ethyl, propyl, butyl, pentyl, hexyl, heptyl, octyl, nonyl, decyl, dodecyl, and the like; aryls such as phenyl, naphthyl, anthracyl, tolyl, ethylphenyl, 1-ethyl-3-methylpentyl, 1-methylheptyl, and the like; cycloalkyls such as cyclobutyl, cyclopentyl, cyclohexyl, cyclooctyl, and the like. Other examples include allyl and isobutenyl; 1,3,5-sym-triazinyl, 2-benzothiazolyl, 2-benzimidazolyl, 2-benzoxazolyl, 2-pyridyl, 2-pyrimidinyl, 2,5-thiadiazolyl, 2-pyrazinyl, adipyl, glutaryl, succinyl, malonyl, acetyl, acrylyl, methacrylyl, caproyl, 3-mercaptopropionyl, benzoyl, phthaloyl, terephthaloyl, aminocarbonyl, carbethoxy, carbonyl, formyl, and the like. These are merely exemplary radicals and are in no way intended to limit the scope of the invention.

The hydrogen peroxide used in the reaction according to the present invention is typically present in an amount ranging from 1.05 to 2.05 parts per equivalent of phenylenediamine. Use of less than one equivalent will tend to produce blends of quinonediimine and unreacted phenylenediamine. The strength of the hydrogen peroxide can range from 5% to 85%. The strength is preferably between 10% and 35%.

Catalytic agents which are used along with the hydrogen peroxide include, but are not limited to, carbon supported catalysts such as Pt/C and Pd/C; modified activated carbon catalysts such as those produced by removing surface oxides therefrom as set forth in U.S. Pat. No. 4,624,937, the disclosure of which is incorporated herein by reference; water soluble ionic metal catalysts; activated carbon; metal oxides, such as iron oxide ($FeO_2$), manganese oxide ($MnO_2$), and copper (II) oxide ($CuO_2$); and metals, such as silver (Ag).

The catalysts of the present invention cause the conversion reaction in the process according to the present invention. Even in systems where the oxidizing agent, aqueous hydrogen peroxide, is soluble in the solvent solution of phenylenediamine (i.e. acetronitrile in N,N-dimethylformamide) there is no reaction until the catalyst is added. It is advantageous to utilize solid catalysts in the reaction according to the present invention as there is ease in recovery of the solid catalysts, via filtration, and the solid catalysts can be reused in the process. There are also advantages with respect to environmental containment, and there is less likelihood that there will be contamination by the catalyst in the final isolate of quinonediimine. Further, the catalysts give high conversion and excellent selectivity.

The reaction, according to the present invention, takes place in either a homogeneous or two-phase solvent system. Water soluble organic solvents are used for the homogeneous reaction while water insoluble organic hydrocarbon solvents yield the two-phase system. The two-phase system also includes water. The two-phase oxidation system provides ease of separation of the organic components (both quinonediimine and solvent) from the spent aqueous peroxide layer. Organic aprotic solvents useable in the process of the present invention include, but are not limited to, ketones such as acetone, cyclohexanone, 4-methyl-2-pentanone (methyl isobutyl ketone), 5-methyl-2-hexanone, methyl ethyl ketone; aliphatic and aromatic hydrocarbons as such as hexanes, heptanes, toluene, xylenes, nitriles such as acetonitrile; halogenated solvents such as chloroform, dichloromethane, carbon tetrachloride; water soluble solvents such as dimethyl sulphoxide, N-methyl-2-pyrrolidone, sulfolane, dimethylformanide; esters such as ethyl acetate; ethers such as 1,4-dioxan, and mixtures thereof.

The initial phenylenediamine concentration may range in amounts of from 1% to 100% w/v. Preferably, the initial phenylenediamine concentration ranges from 25% to 60% w/v.

The present reaction may take place at temperatures from $-200°$ C. to $150°$ C., preferably from $25°$ C. to $70°$ C., depending on the solvent.

As mentioned above, water soluble ionic metal catalysts can also be used for the conversion reaction according to the present invention. Examples of such water soluble ionic metal catalysts include, but are not limited to, sodium tungstate ($Na_2WO_4$), copper sulfate ($CuSO_4$) and palladuim acetate ($Pd(CH_3CO_2)_2$). However, the use of the aforementioned water soluble ionic metal catalysts causes a reduction in the selectivity of the quinonediimine formation along with a potential for product contamination due to incomplete separation or product complexation with these cations. Additionally, the water soluble catalysts produce an aqueous stream containing the metal catalysts which can create environmental concerns.

A phase-transfer catalyst may be utilized to accelerate the rate of reaction with the above mentioned water soluble metal catalysts. The addition of tricaprylmethylammonium chloride (Aliquat® 336, Henkle Corp.) to the sodium tungstate/hydrogen peroxide system increases in the rate of conversion of the quinonediimine from the corresponding phenylenediamine.

A phase transfer catalyst can be added directly to the reaction mixture or it can be dissolved in one of the reagents such as Santoflex® 6PPD. The phase transfer catalyst may also be dissolved in a solvent used in the process or in water before addition to the reaction mass.

Another means by which the rate of reaction may be increased is by increasing the stirring or mixing rate in the reaction. By increasing the stirring or mixing, the reaction rate may be effectively adjusted to proceed at a faster pace when necessary.

The present invention can be more clearly illustrated by the following examples.

EXAMPLE 1

A mixture of 20.0 g. of N-1,3-dimethylbutyl-N'-phenyl-p-phenylenediamine (Santoflex® 6PPD) and 40.0 g. of acetonitrile was charged to a 250 ml. flask equipped with an efficient stirrer. A water bath was used to heat and maintain the temperature of this mixture at 35° C. After the solids dissolved, catalyst (0.50 g. of 3% Pt/C with 43.5% $H_2O$ (Johnson Matthey)) was added and hydrogen peroxide (7.8 g. 30–35% in 12.2 g. $H_2O$) was metered into the flask over a 30 min. period. The mixture was allowed to stir for an additional 10 min. and then filtered to remove the solid platinum catalyst. The catalyst was rinsed with 5.0 g of acetonitrile. The quinonediimine was isolated by removing the acetonitrile/water mixture under vacuum. The isolated quinonediimine weighed 19.8 g. and assayed (HPLC) 99.2% with 0.6% 6PPD. The air dried catalyst weighed 0.41 g.

EXAMPLE 2

A mixture of 20.0 g. of N-1,3-dimethylbutyl-N'-phenyl-p-phenylenediamine (Santoflex® 6PPD) and 20.0 g. of N,N-dimethylformamide (DMF) was charged to a 250 ml. flask equipped with an efficient stirrer. A water bath was used to maintain the temperature of the mixture at 35° C. Catalyst (0.51 g. of 3% Pt/C with 43.5% $H_2O$ (Johnson Matthey)) was added after the 6PPD dissolved. Hydrogen peroxide (7.8 g. 30–35% in 12.2 g. $H_2O$) was metered into the stirred mixture over a 30 min. period. This mixture was filtered to remove the platinum catalyst and two 5.0 g. rinses of DMF was used to wash the catalyst.

The filtered mixture was added to 75.0 g. of water and placed in a separatory funnel. After extraction and layer separation, 19.3 g. of quinonediimine was isolated. The HPLC analysis of this isolated product revealed 98.2% quinonediimine and 0.8% 6PPD. There was a very small amount (<0.5%) of DMF that remained in the isolated quinonediimine. The isolated air dried catalyst weighed 0.28 g.

EXAMPLE 3

A mixture of 80.0 g. of N-1,3-dimethylbutyl-N'-phenyl-p-phenylenediamine (Santoflex® 6PPD) and 80.0 g. of heptane was charged to a 500 ml. flask equipped with an efficient stirrer. A water bath was used to maintain the temperature of the mixture at 35° C. Catalyst (1.50 g. of 3% Pt/C with 43.5% $H_2O$ (Johnson Matthey)) was added when the 6PPD dissolved in the heptane. Hydrogen peroxide (62.4 g. 30–35% in 57.6 g. $H_2O$) was metered into the stirred mixture over a 2 hour period. This mixture was filtered to remove the platinum catalyst and two 10.0 g. rinses of heptane was used to wash the catalyst. The quinonediimine was isolated by removing the water layer and recovering the heptane under vacuum on a rotovap. The isolated quinonediimine weighed 79.4 g. and analyzed (HPLC) was 99.5% with no detectable 6PPD. The air dried catalyst weighed 1.29 g.

EXAMPLE 4

A mixture of 20.0 g. of N-1,3-dimethylbutyl-N'-phenyl-p-phenylenediamine (Santoflex® 6PPD) and 40.0 g. of heptane was charged to a 250 ml. flask equipped with an efficient stirrer. A water bath was used to maintain the temperature of the mixture at 55° C. Catalyst (0.50 g. of 3% Pd (unreduced)/C with 55.2% $H_2O$ (Engelhard)) was added to the dissolved mixture. Hydrogen peroxide (15.8 g. 30–35% in 24.2 g. $H_2O$) was metered into the stirred mixture over a 45 min. period and allowed to stir for an additional 30 min. This mixture was filtered and the palladium catalyst was washed with 5.0 g. of heptane. The aqueous layer was removed and the quinonediimine was isolated under vacuum by heptane removal. The isolated product weighed 19.7 g. and analyzed (HPLC) as 97.6% quinonediimine with 1.2% 6PPD present.

EXAMPLE 5

A mixture of 20.0 g. of N-1,3-dimethylbutyl-N'-phenyl-p-phenylenediamine (Santoflex® 6PPD) and 40.0 g. of heptane was charged to a 250 ml. flask equipped with an efficient stirrer and a reflux condenser. A water bath was used to maintain the temperature of the mixture between 80° C. and 85° C. Catalyst (0.75 g. copper (II) oxide (powder)) was added to the dissolved mixture. Hydrogen peroxide (15.8 g. 30–35% in 24.2 g. $H_2O$) was metered in over a 90 min. period. The copper catalyst was removed by filtration and washed with 5.0 g. heptane. The aqueous layer was removed and the heptane was recovered under vacuum leaving 19.9 g. of isolated quinonediimine. Analysis (HPLC) revealed 95.7% quinonediimine with 3.2% unreacted 6PPD. The copper (II) oxide was quantitatively recovered.

Other phenylenediamines, including Santoflex® 77PD [$R_1=R_2$=1,4-dimethylpentyl, $R_3$=hydrogen], Santoflex® 14 [$R_1$=phenyl, $R_2$=1,4-dimethylpentyl, $R_3$=hydrogen], Santoflex® IPPD, [$R_1$=phenyl, $R_2$=isopropyl, $R_3$=hydrogen], Santoflex® 44PD [$R_1=R_2$=sec-butyl, $R_3$=hydrogen], 4-aminodiphenylamine [$R_1$=H, $R_2$=phenyl, $R_3$=hydrogen], N,N'-diphenyl-para-phenylenediamine [$R_1=R_2$=phenyl, $R_3$=hydrogen] and N-cyclohexyl-N'-phenyl-para-phenylenediamine [$R_1$=cyclohexyl, $R_2$=phenyl, $R_3$=hydrogen] can be utilized in the process of the present invention.

The quinonediimines prepared by the process of the present invention exhibit multiple activities in vulcanized elastomers. These activities include long term antioxidant activity, along with antiozonant capacity. In fact, the antioxidant capacity of these antidegradants persists even after the vulcanizate has been extracted with solvents. In addition, quinonediimines provide these benefits without the negative effect on scorch generally associated with para-phenylenediamine antidegradants common to the industry. A summary of the activities of these compounds in rubber can be found in the literature, (Cain, M. E. et al., *Rubber Industry*, 216–226, 1975).

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the invention, it is claimed:

1. A process for preparing a quinonediimine by reacting a corresponding phenylenediamine with hydrogen peroxide in the presence of a catalyst.

2. The process of claim 1 wherein the catalyst is a solid catalyst selected from a palladium/carbon (Pd/C), platinum/carbon (Pt/C), iron oxide ($FeO_2$), copper (II) oxide ($CuO_2$), manganese oxide ($MnO_2$), silver (Ag), a water soluble ionic metal catalyst, activated carbon or a modified activated carbon catalyst said modified activated carbon catalyst characterized by having surface oxides removed therefrom.

3. The process of claim 1 wherein the phenylenediamine is an ortho- or para-phenylenediamine of the following Formula I:

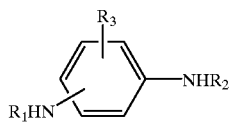

wherein $R_1$ and $R_2$ and $R_3$ are the same or different and are selected from hydrogen, hydroxyl, halogen, alkyl, alkoxy, aryl, aralkyl, alkaryl, cycloalkyl, heterocycle, acyl, aroyl, carbamyl, carboxylic acids, esters, ethers, ketones, alcohols, thiols, alkylthiols, and cyano, and further wherein the resulting corresponding quinonediimine is of the following Formula IIa or IIb:

Formula IIa

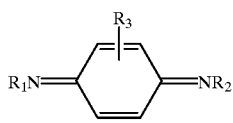

Formula IIb

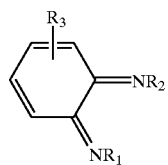

wherein $R_1$, $R_2$ and $R_3$ and are the same as in the compound of Formula I.

4. The process of claim 3 wherein $R_1$=1,3-dimethylbutyl, $R_2$=phenyl, and $R_3$=hydrogen.

5. The process of claim 4 wherein the compound of Formula I is N-1,3-dimethylbutyl-N'-phenyl-p-phenylenediamine.

6. The process of claim 3 wherein the quinonediamine is a para-quinonediamine.

7. The process of claim 6 wherein $R_1$ and $R_2$=1,4-dimethylpentyl, and $R_3$=hydrogen.

8. The process of claim 6 wherein $R_1$, and $R_2$ are selected from isopropyl, sec-butyl, cyclohexyl, phenyl, and hydrogen.

9. The process of claim 1 wherein the reaction takes place in the presence of a solvent system selected from a homogeneous or a two-phase solvent system.

10. The process of claim 9 wherein the solvent is a two phase solvent system comprising a water insoluble organic solvent in combination with water.

11. The process of claim 9 wherein the solvent system is a homogeneous solvent system comprising one or more water soluble organic solvents.

12. The process of claim 10 wherein the water insoluble organic solvent comprises hexanes.

13. The process of claim 11 wherein the water soluble solvents are selected from acetonitrile and dimethylformamide (DMF).

14. The process of claim 1 wherein the reaction takes place at a temperature of between 25° C. and 70° C.

15. The process of claim 1 wherein the hydrogen peroxide is present in an amount ranging from about 1.05 to about 2.05 parts per equivalent of phenylenediamine.

16. The process of claim 1 wherein the strength of the hydrogen peroxide is between 10% and 35%.

17. A process for preparing a quinonediimine by reacting the corresponding phenylenediamine with hydrogen peroxide in the presence of a catalyst wherein the phenylenediamine is an ortho- or para-phenylenediamine of the following Formula I:

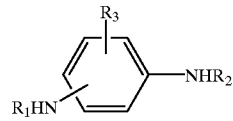

wherein $R_1$, $R_2$ and $R_3$ are the same or different and are selected from hydrogen, hydroxyl, halogen, alkyl, alkoxy, aryl, aralkyl, alkaryl, cycloalkyl, heteroocycle, acyl, aroyl, carbamyl, carboxylic acids, esters, ethers, ketones, alcohols, thiols, alkylthiols, and cyano, and further wherein the resulting corresponding quinonediimine is of the following Formula IIa or IIb:

Formula IIa

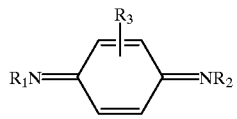

Formula IIb

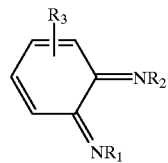

wherein $R_1$, $R_2$ and $R_3$ are the same as in the compound of Formula I, wherein the reaction takes place in a homogenous solvent system or in a two-phase solvent system comprising a water insoluble organic solvent and water.

18. The process of claim 17 wherein the homogeneous solvent is selected water soluble organic solvents.

19. The process of claim 18 wherein the water soluble organic solvent is selected from acetonitrile and dimethylformamide (DMF).

20. The process of claim 17 wherein the water insoluble organic solvent of the two phase solvent system comprises hexanes.

21. The process of claim 17 wherein the catalyst is a solid catalyst selected from a palladium/carbon (Pd/C), platinum/carbon (Pt/C), iron oxide ($FeO_2$), copper (II) oxide ($CuO_2$), manganese oxide ($MnO_2$), silver (Ag), a water soluble ionic metal catalyst, activated carbon or a modified activated carbon catalyst said modified activated carbon catalyst characterized by having surface oxides removed therefrom.

22. The process of claim 17 wherein the compound of Formula I is N-1,3-dimethylbutyl-N'-phenyl-p-phenylenediamine.

* * * * *